United States Patent [19]

Klioze

[11] 3,996,354

[45] Dec. 7, 1976

[54] 1,3-DIHYDRO-1'-DIMETHYLPHOSPHINY-LALKYL-3-PHENYLSPIRO(ISOBEN-ZOFURAN)S

[75] Inventor: Solomon S. Klioze, Flemington, N.J.

[73] Assignee: American Hoechst Corporation, Bridgewater, N.J.

[22] Filed: Jan. 26, 1976

[21] Appl. No.: 652,150

[52] U.S. Cl. .............................. 424/200; 424/203; 424/267; 424/274; 424/285; 260/293.58; 260/346.2 R; 260/326.5 A

[51] Int. Cl.² ...................................... C07D 491/10

[58] Field of Search ............... 260/293.66, 326.5 A, 260/346.2 R, 293.58; 424/200

[56] References Cited

UNITED STATES PATENTS 3,959,475   5/1976   Bauer et al. .................. 260/293.58

*Primary Examiner*—Henry R. Jiles
*Assistant Examiner*—Robert T. Bond
*Attorney, Agent, or Firm*—Curtis, Morris & Safford

[57] ABSTRACT

Novel 1,3-dihydro-1'-dimethylphosphinylalkyl-3-phenylspiro[isobenzofuran]s and methods of preparing the same are described. These compounds are useful as antidepressants.

19 Claims, No Drawings

1,3-DIHYDRO-1'-DIMETHYLPHOSPHINYLAL-KYL-3-PHENYLSPIRO(ISOBENZOFURAN)S

This invention relates to novel 1,3-dihydro-1'-dimethylphosphinyl-alkyl-3-phenylspiro[isobenzofuran]s and pharmaceutically acceptable salts thereof which are useful as antidepressants, to a method of preparing the same, to a method of treatment of depression with pharmaceutically effective amounts thereof, and to pharmaceutical compositions containing such compounds as essential active ingredients.

To the best of my knowledge, the compounds of this invention have not heretofore been described or suggested. Spiro[phthalan-piperidine]s described by W. J. Houlihan et al. in U.S. Pat. No. 3,686,186, 1,3-dihydrospiro[isobenzofuran]s described by Bauer and Kosley in U.S. patent application Ser. No. 424,080 filed Dec. 12, 1973, now U.S. Pat. No. 3,962,259 substituted 1,3-dihydro[isobenzofuran]s described by Bauer and Kosley in U.S. patent application Ser. No. 502,650 filed Sept. 3, 1974, now U.S. Pat. No. 3,959,475, and 1,3-dihydro-3-phenyl-1'-(2-propynyl)spiro[isobenzofuran]s described by Duffy in U.S. Pat. application Ser. No. 596,163 filed July 15, 1975 are outside the scope of this invention.

The same applies to the natural product of the formula

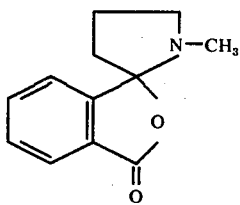

described by y. Inushubi et al. [Chem. and Pharm. Bull. (Japan), 12, 749 (1964)].

The compounds of the present invention which differ significantly from the prior art compounds possess unexpected antidepressant activity.

It has been widely recognized that very special chemical structure requirements are essential for a substance to pass the mysterious blood brain barrier in order to be able to enter the central nervous system. Many of the antidepressant agents currently in use, for example, are strongly lipophilic in nature and it is generally assumed that this is an essential structural or physical property requirement for entrance into the brain. It is therefore surprising to find that the compounds of this invention possessing the highly polar phosphinyl radical readily pass the blood brain barrier to produce an antidepressant effect. It is further surprising that the presence of a highly polar group on the basic nitrogen does not interfer with the antidepressant activity. The good activity of the compounds of the invention is unanticipated inasmuch as it is generally recognized that a basic nitrogen bearing small lipophilic substituents, such as a methyl group, is essential for good antidepressant activity.

This invention relates to novel 1,3-dihydro-1'-dimethylphosphinylalkyl-3-phenylspiro[isobenzofuran]s of the formula

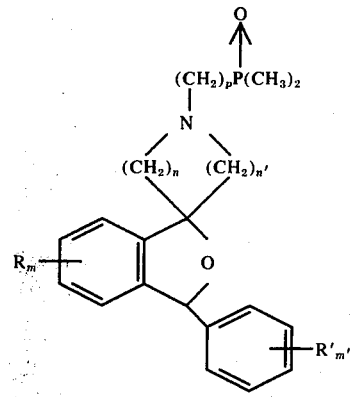

wherein R and R' are hydrogen, lower alkyl, lower alkoxy, halogen or hydroxy; $m$ and $m'$ are the integers 1 or 2; $n$ and $n'$ are integers from 1 to 3 with the sum of $n$ and $n'$ being 3, 4 or 5; $p$ is an integer from 1 to 4; and the pharmaceutically acceptable acid addition salts thereof. The terms "lower alkyl" and "lower alkoxy" are intended to include alkyl and alkoxy of from 1 to 6 carbon atoms.

Preferred embodiments of the present invention are those wherein the sum of $n$ and $n'$ is 4, $p$ is 1 and R and $R^1$ are hydrogen, alkyl of 1 to 3 carbon atoms, alkoxy of 1 to 4 carbon atoms, halogen or hydroxy.

Acids useful for preparing the pharmaceutically acceptable acid addition salts of this invention include inorganic acids such as hydrochloric, hydrobromic, sulfuric, nitric, phosphoric and perchloric, as well as organic acids such as tartaric, citric, acetic, succinic, maleic, fumaric and oxalic acids.

The compounds of the present invention are prepared by the addition of a halogenated alkyl dimethyl phosphine oxide of the formula

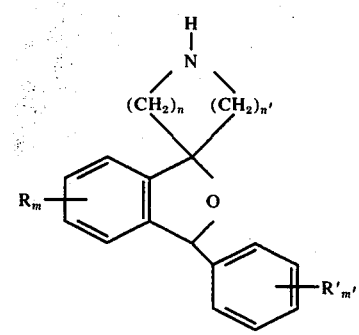

wherein X is chlorine or bromine and $q$ is an integer from 0 to 3 to a 1,3-dihydro-3-phenylspiro[isobenzofuran-cycloazalkane] of the formula

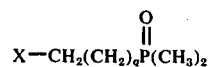

in the presence of an organic solvent and an acid scavenger at a temperature from ambient to the reflux point of the reaction mixture. The 1,3-dihydro-3-phenylspiro[isobenzofuran]s starting materials are described in U.S. application Ser. No. 502,650, cited above. In a preferred method dimethylformamide is utilized as the solvent and potassium carbonate as the acid scavenger at a temperature of 100° C. Compounds in which R or $R^1$ are hydroxy are prepared by dealkylation of corresponding alkoxy compounds of the invention by methods known to the art. A preferred method is the treatment of such alkoxy compounds with an acid, such as hydrobromic acid or aluminum tribromide, under the normal conditions of hydrolyzing reactions.

Compounds of the present invention are useful in the treatment of depression in mammals, as demonstrated by their ability to inhibit tetrabenazineinduced depression in mice [International Journal of Neuropharmacology, 8, 73 (1969)], a standard assay for useful antidepressant properties. Thus, for example, 1,3-dihydro-1'-dimethylphosphinylmethyl-3-phenylspiro[isobenzofuran-1,4'-piperidine].hemihydrate effects a 50% inhibition of ptosis of tetrabenzazine-induced depression at the intraperitoneal dose of 4.05 mg/kg of body weight. This datum indicates that compounds of the present invention are useful in treatment of depression in mammals when administered in amounts ranging from 0.1 to about 50 mg per kg of body weight per day.

Illustrative examples of compounds of the invention are:

1,3-dihydro-1'-dimethylphosphinylmethyl-6-fluoro-3-phenylspiro[isobenzofuran-1,4'-piperidine];

1,3-dihydro-1'-[2-(dimethylphosphinyl)ethyl]-3-(4-fluorophenyl)spiro[isobenzofuran-1,4'-piperidine];

1,3-dihydro-3-(3,4-dimethoxyphenyl)-1'-(dimethylphosphinylmethyl)spiro[isobenzofuran-1,4'-piperidine];

1,3-dihydro-1'-[(3-dimethylphosphinyl)propyl]-3-phenylspiro[isobenzofuran-1,4'-piperidine];

1,2',3,3',4',5',6',7'-octahydro-1'-dimethylphosphinylmethyl-3-phenylspiro[isobenzofuran-1,4'-azepine];

1,3-dihydro-1'-dimethylphosphinylmethyl-3-phenyl-5-propoxyspiro[isobenzofuran-1,4'-piperidine];

1,3-dihydro-1'-[2-(dimethylphosphinyl)ethyl]-3-(4-ethylphenyl)spiro[isobenzofuran-1,4'-piperidine]; and 1,3-dihydro-1'-[(4-dimethylphosphinyl)butyl]-6-isopropyl-3-phenylspiro[isobenzofuran-1,4'-piperidine].

Effective quantitites of the compounds of the invention may be administered to a patient by any one of various methods, for example, orally as in capsules or tablets, parenterally in the form of sterile solutions or suspension, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

Tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated into solutions or suspensions. These preparations should contain at least 0.1% of active compound, but this may be varied to be between 0.5 and about 30% of the weight thereof. The amount of active compound in such compositions is such that an effective dosage will be obtained. Preferred compositions and preparations according to the present invention are prepared so that parenteral dosage units contain between 0.5 to 100 milligrams of active compound.

The solutions or suspensions may also include the following components: sterile diluents such as water for injection, saline solutions, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple dose vials made of glass or plastic.

EXPERIMENTAL 3.0 g of anhydrous potassium carbonate and 1.39 g of chloromethyl dimethyl phosphine oxide are added to a solution of 2.65 g of 1,3-dihydro-3-phenylspiro[isobenzofuran-1,4'-piperidine] in 40 ml of dimethylformamide. The resulting suspension is heated under nitrogen at 100° C for 20 hours. The reaction mixture is permitted to cool, diluted with 400 ml of benzene and then washed with water. The organic layer is separated and dried and the solvent is evaporated off, leaving an orange oil. The oil is triturated with an ether-petroleum ether (4:1) mixture and then cooled to give faintly yellow crystals which are recrystallized from a benzene-hexane mixture to form a nearly colorless crystalline solid, mp 96°–99° C, of 1,3-dihydro-1'-dimethylphosphinylmethyl-3-phenylspiro[isobenzofuran-1,4'-piperidine]hemihydrate.

Analysis: Calculated for $C_{21}H_{26}NO_2P \cdot \frac{1}{2}H_2O$: 69.21%C; 7.47%H; 3.48%N. Found: 69.14%C; 7.05%H; 3.87%N.

In analogous manner, 1,3-dihydro-3-phenyl-spiro[isobenzofuran-1,3'-pyrrolidine], 1,3-dihydro-3-phenylspiro[isobenzofuran-1,3'-piperidine], 1,3-dihydro-6-methoxy-3-phenylspiro[isobenzofuran-1,4'-piperidine], 1,3-dihydro-5-methoxy-3-phenyl-spiro[isobenzofuran-1,4'-piperidine], 1,3-dihydro-3-(4-tolyl)spiro[isobenzofuran-1,4'-piperidine], 1,3-dihydro-3-(4-methoxyphenyl)spiro[isobenzofuran-1,4'-piperidine] and 1,3-dihydro-3-(4-fluorophenyl)-spiro[isobenzofuran-1,4'-piperidine] are treated to provide 1,3-dihydro-1'-dimethylphosphinylmethyl-3-phenylspiro[isobenzofuran-1,3'-pyrrolidine], 1,3-dihydro-1'-dimethylphosphinylmethyl-3-phenyl-spiro[isobenzofuran-1,3'-piperidine], 1,3-dihydro-1'-dimethylphosphinylmethyl-6-methoxy-3-phenyl-spiro[isobenzofuran-1,4'-piperidine], 1,3-dihydro-1'-dimethylphosphinylmethyl-5-methoxy-3-phenyl-spiro[isobenzofuran-1,4'-piperidine], 1,3-dihydro-1'-dimethylphosphinylmethyl-3-(4-tolyl)spiro[isobenzofuran-1,4'-piperidine], 1,3-dihydro-1'-dimethylphosphinylmethyl-3-(4-methoxyphenyl)spiro[isobenzofuran-1,4'-piperidine] and 1,3-dihydro-1'-dimethylphosphinylmethyl-3-(4-fluorophenyl)spiro[isobenzofuran-1,4'-piperidine], respectively.

Similarly the treatment of 1,3-dihydro-3-phenylspiro[isobenzofuran-1,4'-piperidine] with 2-chloroethyl dimethylphosphine oxide and 3-chloropropyl dimethylphospine oxide produces 1,3-dihydro-1'[2-(dimethylphosphinyl)ethyl]-3-phenylspiro[isobenzofuran-1,4'-piperidine] and 1,3-dihydro1'-[3-(dimethylphosphinyl)propyl]-3-phenylspiro(isobenzofuran-1,4'-piperidine), respectively.

A solution of 1,3-dihydro-1'-dimethylphosphinylmethyl-6-methoxy-3-phenylspiro[isobenzofuran-1,4'-piperidine] and 48% hydrobromic acid is heated under reflux, cooled, diluted with water, neutralized with sodium bicarbonate and extracted with chloroform. The chloroform solution is dried and the chloroform evaporated off, affording 1,3-dihydro-1'-dimethylphosphinylmethyl-6-hydroxy-3-phenylspiro[isobenzofuran-1,4'-piperidine]. In an analogous manner, 1,3-dihydro-1'-dimethylphosphinylmethyl-5-methoxy-3-phenyl-spiro[isobenzofuran-1,4'-piperidine] and 1,3-dihydro-1'-dimethylphosphinylmethyl-3-(4-methoxyphenyl)-spiro[isobenzofuran-1,4'-piperidine] are treated to provide 1,3-dihydro-1'-dimethylphosphinylmethyl-5-hydroxy-3-phenylspiro[isobenzofuran-1,4'-piperidine] and 1,3-dimethylphosphinylmethyl-3-(4-hydroxyphenyl)spiro[isobenzofuran-1,4'-piperidine], respectively.

I claim:
1. A compound of the formula

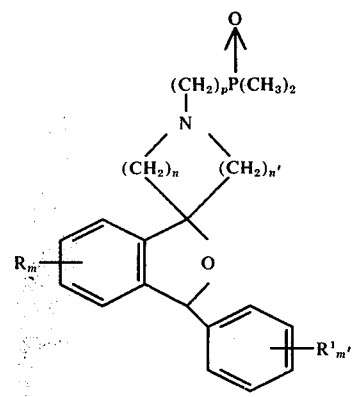

wherein R and R¹ are hydrogen, lower alkyl, lower alkoxy, halogen or hydroxy; $m$ and $m'$ are the integers 1 or 2; $n$ and $n'$ are integers from 1 to 3 with the sum of $n$ and $n'$ being 3,4 or 5; $p$ is an integer from 1 to 4; and the pharmaceutically acceptable acid addition salts and hydrates thereof.

2. A compound as defined in claim 1 wherein R and R¹ are hydrogen and $m$ and $m'$ are 0 or 1.
3. A compound as defined in claim 2 wherein $p$ is 1.
4. A compound as defined in claim 2 wherein R and R¹ are hydrogen, alkyl of from 1 to 3 carbon atoms, alkoxy of from 1 to 4 carbon atoms, halogen or hydroxy.
5. A compound as defined in claim 4 wherein $n$ and $n'$ are integers from 1 to 3 with the sum of $n$ and $n'$ being 3 or 4.
6. A compound as defined in claim 5 wherein $p$ is 1.
7. A compound as defined in claim 1 wherein R and R¹ are hydrogen, methyl, methoxy, chlorine, fluorine or hydroxy; $m$ and $m'$ are 1 and $n$ and $n'$ are integers from 1 to 3 with the sum of $n$ and $n'$ being 3 or 4.
8. A compound as defined in claim 7 wherein the sum of $n$ and $n'$ is 4.
9. A compound as defined in claim 7 wherein $p$ is 1.
10. A compound as defined in claim 1 wherein $p$ is 1.
11. The compound defined in claim 1 which is 1,3-dihydro-1'-dimethylphosphinylmethyl-3-phenyl-spiro[isobenzofuran-1,4'-piperidine].
12. The compound defined in claim 1 which is 1,3-dihydro-1'-dimethylphosphinylmethyl-3-phenyl-spiro[isobenzofuran-1,3'-pyrrolidine].
13. The compound defined in claim 1 which is 1,3-dihydro-1'-dimethylphosphinylmethyl-3-phenyl-spiro[isobenzofuran-1,3'-piperidine].
14. The compound defined in claim 1 which is 1,3-dihydro-1'-dimethylphosphinylmethyl-6-hydroxy-3-phenylspiro[isobenzofuran-1,4'-piperidine].
15. The compound defined in claim 1 which is 1,3-dihydro-1'-dimethylphosphinylmethyl-5-hydroxy-3-phenylspiro[isobenzofuran-1,4'-piperidine].
16. The compound defined in claim 1 which is 1,3-dihydro-1'-dimethylphosphinylmethyl-3-(4-fluorophenyl)spiro[isobenzofuran-1,4'-piperidine].
17. The compound defined in claim 1 which is 1,3-dihydro-1'-dimethylphosphinylmethyl-3-(4-hydroxyphenyl)spiro[isobenzofuran-1,4'-piperidine].
18. A method of treating depression which comprises administering to a patient a pharmaceutically effective amount of a compound defined in claim 1.
19. A anti-depressant composition which comprises between about 0.5 and 70 percent by weight of a compound defined in claim 1 as an active ingredient, the balance being a pharmaceutically acceptable carrier therefor.

* * * * *

UNITED STATES PATENT AND TRADEMARK OFFICE
CERTIFICATE OF CORRECTION

PATENT NO. : 3,996,354
DATED : December 7, 1976
INVENTOR(S) : Solomon S. Klioze

It is certified that error appears in the above-identified patent and that said Letters Patent are hereby corrected as shown below:

Column 1, line 41, change "y" to "Y";

Column 2, reverse the second and third structures;

Column 3, line 11, change "tetrabenazineinduced" to

--tetrabenazine-induced--;

Column 5, line 36, change "dihydrol'" to --dihydro-1'--.

Signed and Sealed this

Eighth Day of March 1977

[SEAL]

Attest:

RUTH C. MASON
*Attesting Officer*

C. MARSHALL DANN
*Commissioner of Patents and Trademarks*